United States Patent
Domnik et al.

(10) Patent No.: US 11,565,129 B2
(45) Date of Patent: Jan. 31, 2023

(54) BINARY TRACKING OF AN ANATOMICAL TRACKING STRUCTURE ON MEDICAL IMAGES

(71) Applicant: Brainlab AG, Munich (DE)

(72) Inventors: Birte Domnik, Munich (DE); Kajetan Berlinger, Munich (DE)

(73) Assignee: BRAINLAB AG, Munich (DE)

(*) Notice: Subject to any disclaimer, the term of this patent is extended or adjusted under 35 U.S.C. 154(b) by 353 days.

(21) Appl. No.: 16/070,112

(22) PCT Filed: Jun. 13, 2017

(86) PCT No.: PCT/EP2017/064396
§ 371 (c)(1),
(2) Date: Jul. 13, 2018

(87) PCT Pub. No.: WO2018/228673
PCT Pub. Date: Dec. 20, 2018

(65) Prior Publication Data
US 2021/0213304 A1    Jul. 15, 2021

(51) Int. Cl.
*A61N 5/10* (2006.01)
*G16H 20/40* (2018.01)
(Continued)

(52) U.S. Cl.
CPC .............. *A61N 5/1049* (2013.01); *A61N 5/10* (2013.01); *A61N 5/103* (2013.01); *A61N 5/107* (2013.01);
(Continued)

(58) Field of Classification Search
CPC ........ A61N 5/10; A61N 5/103; A61N 5/1037; A61N 5/1038; A61N 5/1048;
(Continued)

(56) References Cited

U.S. PATENT DOCUMENTS 5,446,548 A * 8/1995 Gerig ................. A61B 6/08
250/462.1
6,721,590 B2 * 4/2004 Ohishi .................. A61B 6/466
600/431
(Continued)

FOREIGN PATENT DOCUMENTS

EP        3110331 A1    1/2017
WO    WO2017001441    1/2017

OTHER PUBLICATIONS

Brock, et al. "Use of image registration and fusion algorithms and techniques in radiotherapy: Report of the AAPM Radiation Therapy Committee Task Group No. 132" Medical Physics, vol. No. 7. May 23, 2017.
(Continued)

*Primary Examiner* — Allen C. Ho
(74) *Attorney, Agent, or Firm* — Gray Ice Higdon

(57) ABSTRACT

Disclosed is a computer-implemented method for determining a position of an anatomical tracking structure in a tracking image usable for controlling a radiation treatment such as at least one of radiotherapy or radio surgery of a patient, a corresponding computer program, a non-transitory program storage medium storing such a program and a computer for executing the program, as well as a system for the position of an anatomical tracking structure in a tracking image usable for controlling a radiation treatment such as at least one of radiotherapy or radio surgery of a patient, a system comprising an electronic data storage device and the aforementioned computer.

14 Claims, 16 Drawing Sheets

(51) Int. Cl.
*G16H 30/40* (2018.01)
*G06T 5/30* (2006.01)
*G06T 5/40* (2006.01)
*G06V 10/44* (2022.01)
*G06V 10/46* (2022.01)

(52) U.S. Cl.
CPC ......... *A61N 5/1037* (2013.01); *A61N 5/1038* (2013.01); *A61N 5/1048* (2013.01); *A61N 5/1064* (2013.01); *A61N 5/1065* (2013.01); *A61N 5/1067* (2013.01); *A61N 5/1069* (2013.01); *G06T 5/30* (2013.01); *G06T 5/40* (2013.01); *G06V 10/44* (2022.01); *G16H 20/40* (2018.01); *G16H 30/40* (2018.01); *A61N 2005/1061* (2013.01); *A61N 2005/1062* (2013.01); *G06V 10/467* (2022.01); *G06V 2201/03* (2022.01)

(58) Field of Classification Search
CPC .......... A61N 5/1049; A61N 2005/1061; A61N 2005/1062; A61N 5/1064; A61N 5/1065; A61N 5/1067; A61N 5/1069; A61N 5/107
USPC ...................................... 378/65, 62
See application file for complete search history.

(56) References Cited

U.S. PATENT DOCUMENTS

| | | | |
|---|---|---|---|
| 7,327,865 B2 | 2/2008 | Fu et al. | |
| 7,835,493 B2* | 11/2010 | Keall | A61N 5/1042 378/65 |
| 8,005,190 B2* | 8/2011 | Shibuya | A61N 5/1049 378/65 |
| 8,233,686 B2* | 7/2012 | Lee | A61B 6/12 382/128 |
| 8,457,372 B2* | 6/2013 | Fu | A61N 5/1049 382/128 |
| 8,526,700 B2* | 9/2013 | Isaacs | G06T 5/50 382/285 |
| 8,565,377 B2* | 10/2013 | Robar | A61N 5/1031 378/65 |
| 8,597,211 B2 | 12/2013 | Berlinger | |
| 8,718,346 B2* | 5/2014 | Isaacs | G06T 11/60 382/131 |
| 8,992,405 B2* | 3/2015 | Chebrolu | G16H 30/20 378/65 |
| 9,014,424 B2 | 4/2015 | Berlinger et al. | |
| 9,084,888 B2* | 7/2015 | Poulsen | A61N 5/1049 |
| 9,474,493 B2* | 10/2016 | Todor | G06T 7/136 |
| 9,604,077 B2* | 3/2017 | Xing | A61N 5/1049 |
| 9,616,251 B2* | 4/2017 | Filiberti | A61N 5/1077 |
| 9,734,589 B2* | 8/2017 | Yu | A61B 34/20 |
| 9,919,164 B2* | 3/2018 | Taguchi | A61N 5/1067 |
| 11,042,993 B2* | 6/2021 | Berlinger | A61N 5/103 |
| 11,097,129 B2* | 8/2021 | Sakata | G06T 7/75 |
| 11,135,449 B2* | 10/2021 | Johnson | A61N 5/1083 |
| 11,232,319 B2* | 1/2022 | Udupa | G06T 7/136 |
| 11,328,434 B2* | 5/2022 | Terunuma | G06T 7/246 |
| 2008/0037843 A1 | 2/2008 | Fu et al. | |
| 2015/0360056 A1 | 12/2015 | Xing et al. | |

OTHER PUBLICATIONS

Glide-Hurst, et al. "Improving radiotherapy planning, delivery, accuracy, and normal tissue sparing using cutting edge technologies" Journal of Thoracic Disease. Apr. 1, 2014.
International Search Report and Written Opinion issued in PCT Application No. PCT/EP2017/064396 dated Mar. 15, 2018.
Gendrin, et al. "Monitoring tumor motion by real time 2D/3D registration during radiotherapy" Radiotherapy and Oncology. Feb. 2012.

\* cited by examiner

| Term | Explanation |
|---|---|
| reference image | The image which was selected from the image sequence for target identification / template generation. |
| target identification | identification of the tracking structure by fusing the DRR with the reference image |
| DRR | digital rendered radiograph (DRR) of the tracking structure selected in the planning CT |
| tracking structure | structure which will be tracked / searched for |
| search image | The image in which it is searched for the tracking structure. |
| template image | The image which contains the tracking structure. The template image will be used to find the tracking structure in the search image. It is usually smaller than the search image. |
| PBT | Preliminary binary template = DRR |
| CPBT | Corrected preliminary binary template |
| CBRI | Cropped Binary Reference Image, see Section 5.3.3 |
| false positives | pixels which are contained in the PBT but not in the CBRI |
| false negatives | pixels which are not contained in the corrected PBT but in the CBRI |

Fig. 2

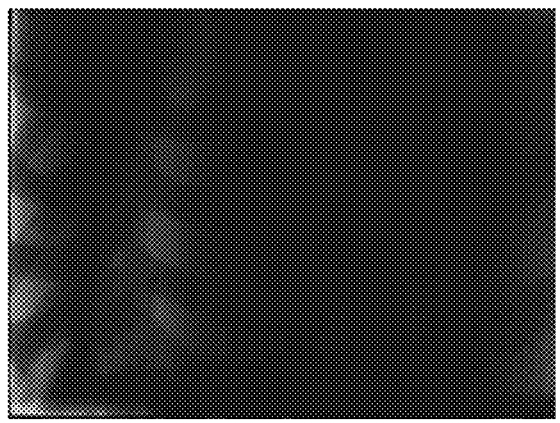
a) Incoming image.
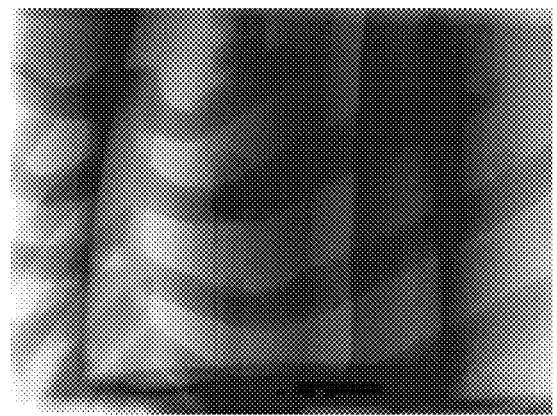
b) After contrast enhancement.
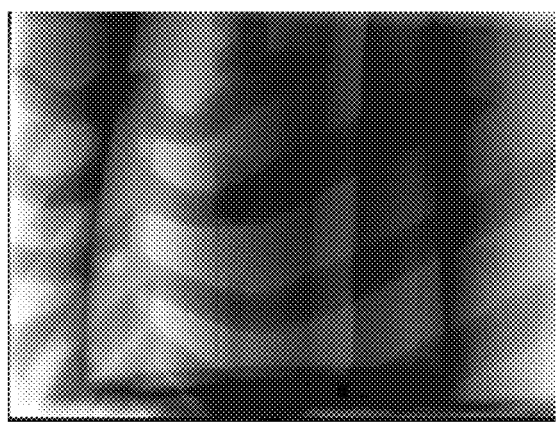
c) After denoising.
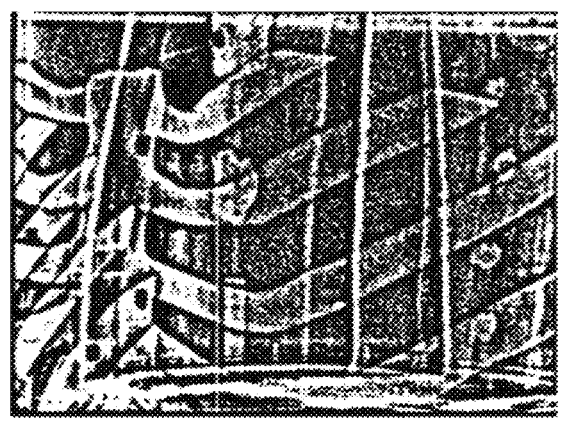
d) After binary filter.
Fig. 7

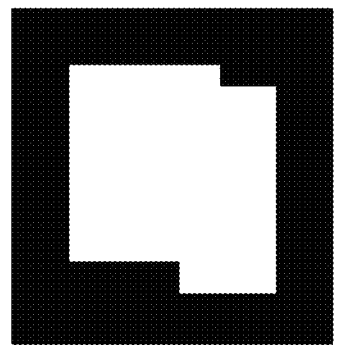
a) Preliminary Binary Template ("PBT")
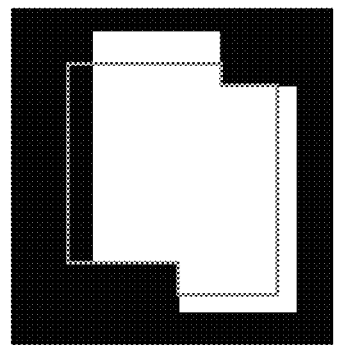
b) Cropped binary reference image ("CBRI") with PBT contour in gray.
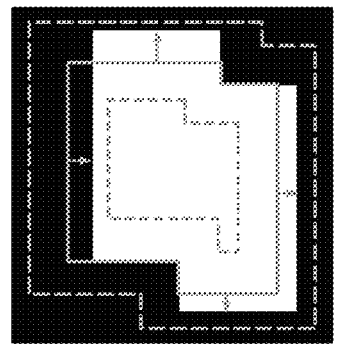
c) Correction of PBT contour along the arrows.
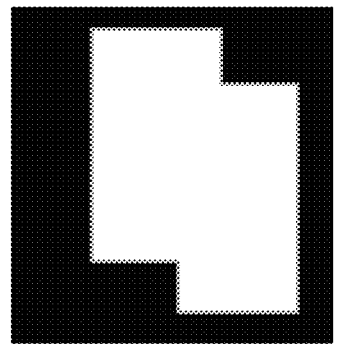
d) Corrected PBT contour = contour of Corrected Binary Template (CBT).
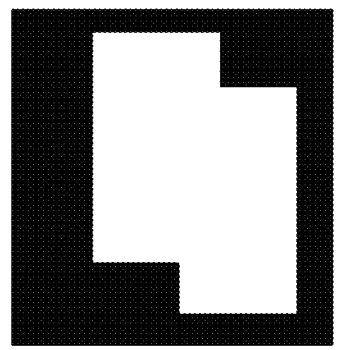
e) CBT = final Binary Template.
Fig. 12

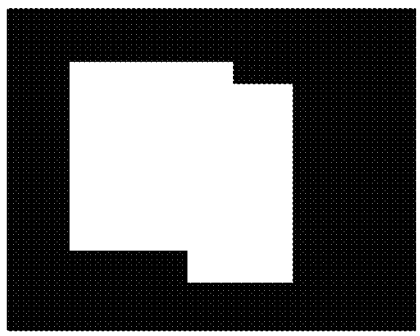
a) Preliminary Binary Template ("PBT")
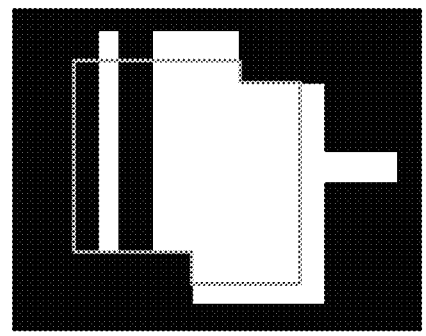
b) Cropped binary reference image ("CBRI") with PBT contour in gray.
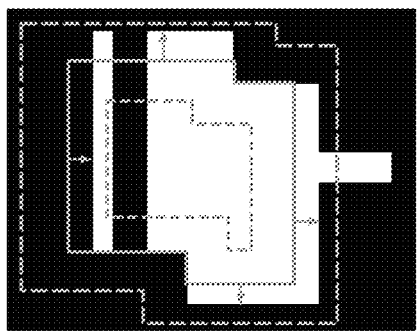
c) Correction of PBT contour along the arrows.
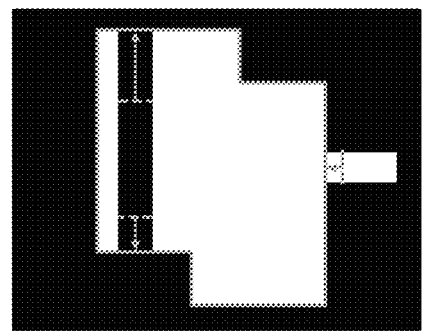
d) Contour estimation.
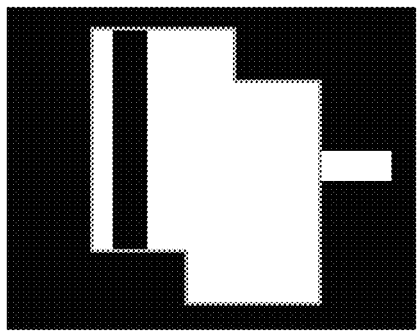
e) Corrected PBT contour = contour of Corrected Binary Template (CBT).
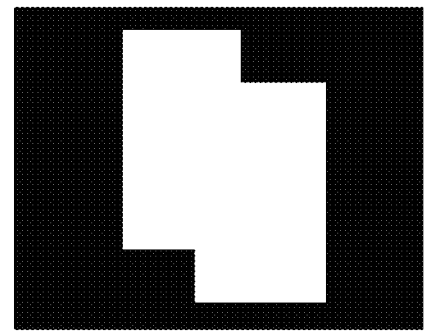
f) CBT = final Binary Template.
Fig. 13

BINARY TRACKING OF AN ANATOMICAL TRACKING STRUCTURE ON MEDICAL IMAGES

The present invention relates to a computer-implemented method for determining the position of an anatomical tracking structure in a tracking image usable for controlling radiation treatment such as at least one of radiotherapy or radiosurgery of a patient, a corresponding computer program, a non-transitory program storage medium storing such a program and a computer for executing the program, as well as a system for the position of an anatomical tracking structure in a tracking image usable for controlling radiation treatment such as at least one of radiotherapy or radiosurgery of a patient, the system comprising an electronic data storage device and the aforementioned computer.

TECHNICAL BACKGROUND

In a given gray-scale image or image sequence we want to track a structure, called "tracking structure". In this application, a tracking algorithm is presented which improves tracking on images where the tracking structure is (partially) occluded by another structure which moves differently than the tracking structure. A possible application of this invention is lung tumour tracking on x-ray images for markerless radiotherapy of lung cancer.

Tracking can be performed with the Template Matching algorithm. Template Matching is a method for searching and finding the location of a template image in a larger search image. The template image contains the tracking structure which will be searched for. The template image is slid over the search image and compared to the patch of the search image under the template image. The comparison results in a similarity value between the patch and the template. A template mask might be provided to the comparison method to weight the pixels in both the template and the patch. The patch which has the highest similarity with the template is considered as detection result. Its position represents the detected point.

The known tracking solutions based on Template Matching are shortly described as follows.

Template Matching on gray-scale images comprises selection of one image from an image sequence which is called "reference image" in this application. The template is given by a (rectangular) patch of the reference image containing the tracking structure. The template contains information about both the tracking structure and occluding structures. Gray values of the tracking structure in the template depend on the location of the occluding structure. The template contains not only the (occluded) tracking structure but also parts of the occlusion outside the tracking structure. This is because a rectangular template is used which in general does not agree with the shape of the tracking structure. Therefore, the template depends on the motion state represented in the selected reference image. The similarity between the template and the corresponding patch of a search image with a motion state different than the one of the reference image is less than the maximum similarity. The difference to the maximum similarity depends on how different the tracking structure and the occluding structure move. Fake structures which are structures different than the tracking structure in the search image with a high similarity to the template might have a higher similarity causing the tracking to fail.

DRR tracking on x-ray images comprises using a digitally rendered/reconstructed radiograph (DRR) of the tracking structure selected in a planning CT as template in a Template Matching algorithm. However, DRR and x-ray are of different modality so that a direct comparison of the images may be difficult. Furthermore, the DRR is artificial and depends on the used rendering algorithm. Also, the DRR is based on planning CT which is potentially outdated as it is acquired typically some days before the first treatment and only once, artefacts are possible due to breathing motion, and a DRR is often non-representative of a specific breathing state (e.g., full inhale or free-breathing).

The present invention is designed to provide an improved method of tracking a target structure in medical image data which delivers more reliable results.

The present invention can be used in connection with a system for image-guided radiotherapy such as VERO® and ExacTrac®, both products of Brainlab AG.

Aspects of the present invention, examples and exemplary steps and their embodiments are disclosed in the following. Different exemplary features of the invention can be combined in accordance with the invention wherever technically expedient and feasible.

Exemplary Short Description of the Present Invention

In the following, a short description of the specific features of the present invention is given which shall not be understood to limit the invention only to the features or a combination of the features described in this section.

The disclosed method encompasses binarizing a reference image and a planning image and selecting in both binarized images a tracking structure including for example a target of radiation treatment (radiotherapy or radiosurgery) such as a tumour. A template for searching for and determining the position of the tracking structure in further images (tracking images) is then generated from the cropped part of the binarized reference image including the tracking structure. Based on the position of the tracking structure determined in the further images, the relative position between the patient (for example, the tracking structure) and a radiation treatment apparatus (e.g. a beam source) can be adjusted to direct the position of the treatment beam onto e.g. the tracking structure.

General Description of the Present Invention

In this section, a description of the general features of the present invention is given for example by referring to possible embodiments of the invention.

In general, the invention reaches the aforementioned object by providing, in a first aspect, a computer-implemented medical data processing method for determining the position of an anatomical tracking structure in a tracking image. In an example, the determined position is usable for at least one of planning or controlling radiation treatment such as at least one of radiotherapy or radiosurgery of a patient. The method comprises executing, on at least one processor of at least one computer (for example at least one computer being part of the navigation system), the following exemplary steps which are executed by the at least one processor.

In a (for example first) exemplary step, planning image data is acquired which describes a planning image of the tracking structure. The tracking structure is an anatomical structure of the patient's body and in one example comprises or consists of the target of the radiation treatment such as a tumour. The planning image for example is a DRR (Digital Rendered/Reconstructed Radiograph) which is rendered from three-dimensional planning image data such as a computed x-ray tomography (CT) or a magnetic resonance tomography (MRT/MR). For creating the DRR, no time series is of the image data is considered. However, a planning CT is often part of a 4D-CT which is a time series of CT scans. In the planning CT, the tracking structure is identified by the user (for example, using a manually operated pointing tool such as a mouse or a stylus for a touch screen). By rendering only this tracking structure, the DRR to be input as the planning image data is obtained. The planning image data is typically generated before the disclosed method is executed, for example some days before the patient is treated, as the medical physicists use the planning image data for generating a radiation treatment plan which tell the radiation treatment system how to irradiate the tumour.

In a (for example second) exemplary step, reference image data is acquired which describes a reference image of the tracking structure. The reference image is for example a two-dimensional x-ray image such as a fluoroscopy which may have been taken with a flat panel x-ray detector system which may be part of the radiation treatment system. For example, a series of such x-ray images is generated from which a user selects one image as the reference image.

In a (for example third) exemplary step, the position of the tracking structure in the reference image is determined. For example, the user identifies the position of the tracking structure in the reference image by defining a tracking template around the image representation of the tracking structure (for example, using a manually operated pointing tool such as a mouse or a stylus for a touch screen). Once the tracking template has been defined, the image series is used to build-up a correlation model which correlates a breathing signal of the patient with the position of the tracking structure. The latter is obtained by detecting the template in every image in the series. The acquisition of the image series and the build-up of the correlation model is a preparation step of the imminent treatment of the patient. For the executing the method according to the first aspect, actually no image series is required. Only one image is needed to create the template.

For example, the position of the tracking structure in the reference image is determined by user interaction or automatically (e.g. by executing an image fusion algorithm on the planning image and the reference image to establish a positional mapping between the—at this instance known—position of the tracking structure in the planning image and the position of a corresponding image constituent in the reference image). If the planning image is an MR image, comparison (e.g. image fusion) with a DRR as the reference image may be supported by using a multimodal atlas which allows transforming an image of a certain modality into its appearance in another modality. For example, the MR image may be matched with the MR section of the multimodal atlas, and the atlas comprises information for mapping MR image appearance values (greyscale values) into x-ray-based image appearance values (greyscale e.g. Hounsfield units), and the x-ray-based/CT section of the multimodal atlas may then be matched with the DRR. The matching may each time be performed by applying an image fusion algorithm to the respective pair of data sets, resulting in positional transformation between the image positions defined in each pair of data sets. The sum (sequential execution) of the two matches will then result in a positional transformation between the image positions in the reference image and the image positions in the planning image, even if they are of different imaging modality. For example, the planning image and the reference image are of different imaging modality, and the planning image and the reference image are each matched with a multimodal atlas configured to match the different imaging modalities onto on another. A positional transformation between the planning image and the reference image can then be established based on the match between the planning image and the multimodal atlas and the match between the reference image and the multimodal atlas.

In a (for example fourth) exemplary step, the reference image is processed to generate a binarized reference image being a binarization of the reference image.

For example, the image processing of the reference image comprises computing, for each pixel in the reference image, a local average of colour values (grey values) in a neighbourhood, for example a predetermined neighbourhood, of each pixel in the reference image, thereby generating a local average image describing the local average for each pixel. In one example, the local average image is compared to, for example subtracted from, the reference image to generate a difference image which describes, for each pixel of the reference image and the local average image, a difference between the colour value of the respective pixel in the reference image and the local average of the respective pixel in the reference image. The average may be weighted according to the distance of the neighbouring pixels from the respective pixel which are included in the calculation of the local average. The region defining the pixels to be included in the calculation of the local average may have a circular or rectangular (for example, square) circumference.

In one example of the disclosed method, a colour value (e.g. grey value) which is contained in the template but not in the selection from the binarized reference image is corrected by adapting the contour of the template to the geometry of the selection from the binarized reference image. This may also be abbreviated as conducting a "false positive correction" of the local average image.

In one example of the disclosed method, a colour value (e.g. grey value) which is contained in the selection from the binarized reference image but not in the template is corrected by adapting the contour of the template to the geometry of the selection from the binarized reference image. This may also be abbreviated as conducting a "false negative correction" of the local average image.

For example, the binarization of the reference image is obtained by thresholding the difference image, for example by thresholding the reference image by colour value (e.g. grey value).

In a (for example fifth) exemplary step, the planning image is processed to generate at least one binarized planning image being a binarization of the at least one of the planning images.

In a (for example sixth) exemplary step, the position of the tracking structure in the binarized planning image is determined and a selection is made from the binarized planning image, wherein the selection includes the tracking structure. In an example, the selection from the binarized planning image includes pixels, for example all pixels, in the binarized planning image having a colour value with a predetermined relationship to a predetermined threshold colour value. This relationship can be acquired by the method according to the first aspect, and the binarized planning image can be filtered accordingly to elect the relevant pixels.

In a (for example seventh) exemplary step, a selection is made from the binarized reference image based on the position of the tracking structure in the reference image, wherein the selection includes the tracking structure. Thereby, a cropped binary reference image (CBRI) is generated.

In a (for example eighth) exemplary step, a template for determining the position of the tracking structure in another image is generated based on the selection from the binarized reference image and the selection from the binarized planning image. The template may be generated according to at least one of the following three examples:

1. The template is generated by manual selection (manual cropping) of the selection from the binarized reference image and the selection from the binarized planning image (for example, by a user using a pointing tool such as a mouse or stylus, e.g. a stylus for use on a touchscreen). The manual selection is supported by the filtering of the reference image leading to a result illustrated by FIG. 7, sub-figure d). As can be seen from that figure, the user is enabled to visually identify an otherwise obscured structure, namely a tumour located behind a rib, so that he can manually define a selection from that image including the tumour representing the tracking structure.

2. The template is generated by matching the binary reference image with the binarized planning image according to the algorithm presented in and described in the context of FIG. 12.

3. The template is generated as described in above example no. 2, but only according to FIG. 12, sub-figure a) (i.e. without using the steps of FIG. 12, sub-figures b) to e)). This is equivalent only generating a preliminary binary template (PBT) without conducting any further matching.

In a (for example ninth) exemplary step, a two-dimensional monochrome (for example, greyscale) image is acquired which describes the tracking structure. The monochrome image is for example a two-dimensional x-ray image such as a fluoroscopy which may have been taken with a flat panel x-ray detector system which may be part of the radiation treatment system. In one example of the method according to the first aspect, a series, for example a plurality, of two-dimensional monochrome images are acquired, each of the monochrome images is processed to generate a binarized monochrome image being a binarization of the respective monochrome image, and the position of the tracking structure in each of the binarized monochrome images is detected by matching the template with the respective binarized monochrome image.

In a (for example tenth) exemplary step, the monochrome image is processed to generate a binarized monochrome image being a binarization of the monochrome image.

In a (for example eleventh) exemplary step, the position of the tracking structure in the binarized monochrome image (i.e. in the binarization of the monochrome image) is detected by matching the template with the binarized monochrome image.

In one example of the method according to the first aspect, a template mask is generated based on the template, wherein the template mask is configured to a pixel to the contour of the template higher the closer the pixel is located to the contour and to weight a pixel having a predetermined distance from a known contour of the template higher than a pixel the having the predetermined distance from an estimated contour of the template. For example, the template mask is generated by morphological dilation and/or morphological erosion of the template.

In examples of the method according to the first aspect, the method comprises at least one of the following steps:
a relative position between an anatomical target of the radiation treatment, for example the tracking structure, and at least part of a radiation treatment system for performing the radiation treatment is adjusted based on the position of the tracking structure in the binarized monochrome image, or
a control signal is determined, based on the position of the tracking structure in the binarized monochrome image, and issued to a treatment beam source of the radiation treatment apparatus for controlling emission of a treatment beam.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. The invention may alternatively or additionally relate to a (physical, for example electrical, for example technically generated) signal wave, for example a digital signal wave, carrying information which represents the program, for example the aforementioned program, which for example comprises code means which are adapted to perform any or all of the steps of the method according to the first aspect.

In a third aspect, the invention is directed to a non-transitory computer-readable program storage medium on which the program according to the fourth aspect is stored.

In a fourth aspect, the invention is directed to at least one computer (for example, a computer), comprising at least one processor (for example, a processor) and at least one memory (for example, a memory), wherein the program according to the fourth aspect is running on the processor or is loaded into the memory, or wherein the at least one computer comprises the computer-readable program storage medium according to the fifth aspect.

In a fifth aspect, the invention is directed to system for determining the position of an anatomical tracking structure in a tracking image usable for controlling radiation treatment such as at least one of radiotherapy or radiosurgery of a patient, the system comprising:
a) the at least one computer according to the preceding claim;
b) at least one electronic data storage device storing at least the planning image data; and
c) a medical imaging device for generating the two-dimensional monochrome image data; and
d) a radiation treatment apparatus comprising a treatment beam source (such as a linear accelerator or a radioactive substance) and a patient support unit (such as a patient couch),
wherein the at least one computer is operably coupled to
the at least one electronic data storage device for acquiring, from the at least one data storage device, at least the planning image data, and
to the medical imaging device for acquiring, from the medical imaging device, the two-dimensional monochrome image and
to the radiation treatment apparatus for issuing a control signal to the radiation treatment apparatus for controlling at least one of
the functionality of the treatment beam source or
the position of the patient support unit on the basis of the position of the tracking structure in the binarized monochrome image.

In general, the invention does not involve or for example comprise or encompass an invasive step which would represent a substantial physical interference with the body requiring professional medical expertise to be carried out and entailing a substantial health risk even when carried out with the required professional care and expertise. For example, the invention does not comprise a step of irradiating the anatomical body part and/or the patient's body with ionizing radiation so that it does not comprise any steps of therapy of the human or animal body, for example it does not comprise any step of radiotherapy or radiosurgery. More particularly, the invention does not involve or in particular comprise or encompass any surgical or therapeutic activity. The invention is instead directed as applicable to positioning a patient relative to the radiation treatment apparatus for example before any radiotherapy or radiosurgery ensues. For this reason alone, no surgical or therapeutic activity and in particular no surgical or therapeutic step is necessitated or implied by carrying out the invention.

It is within the scope of the present invention to combine one or more features of one or more embodiments or aspects of the invention in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can for example be added to said other embodiment.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital light-box. The monitor may also be the monitor of a portable, for example handheld, device such as a smart phone or personal digital assistant or digital media player.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia. The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

The present invention relates to the field of controlling a treatment beam. The treatment beam treats body parts which are to be treated and which are referred to in the following as "treatment body parts". These body parts are for example parts of a patient's body, i.e. anatomical body parts.

Ionising radiation is an example of radiation emittable by the radiation treatment apparatus and is used for example for the purpose of treatment. For example, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation include x-rays, high-energy particles (high-energy particle beams) and/or ionising radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumour are treated using ionising radiation. The tumour is then an example of an anatomical body part.

DESCRIPTION OF THE FIGURES

In the following, the invention is described with reference to the appended figures which give background explanations and represent specific embodiments of the invention. The scope of the invention is however not limited to the specific features disclosed in the context of the figures, wherein

FIGS. 2 to 18 illustrate an implementation of the method according to the first aspect, wherein FIG. 2 defines abbreviations and terminology used;

FIG. 3 is a flow chart for the binary tracking on a single image;

FIG. 4 is a flow chart for the binary tracking on an image sequence;

FIG. 5 is a flow chart for the binary template matching;

FIG. 6 is a flow chart of the image processing;

FIG. 7 is an illustration of the image processing;

FIG. 8 shows the functioning of the binary filter;

FIG. 9 illustrates rendering of a DRR including the tracking structure selected from the planning CT;

FIG. 10 is a flow chart illustrating the identification of the tracking structure (target identification);

FIG. 11 illustrates the computation of an eroded and dilated DRR;

FIG. 12 illustrates the principle of the binary template generation;

FIG. 13 illustrates how to deal with a non-perfect binary reference image (binarized reference image);

FIG. 14 is an illustration of contour estimation;

FIG. 15 is a flow chart of binary template generation by correction of the preliminary binary template (PBT);

FIG. 16 is a flow chart showing the false positive correction;

FIG. 17 is a flow chart showing the false negative correction; and

FIG. 18 is a flow chart showing the computation of the template mask; and

FIG. 1 is a flow diagram illustrating the basic steps of the disclosed method in accordance with the first aspect, which in the illustrative example of FIG. 1 starts with a step S11 of acquiring the planning image data. In subsequent step S12, the reference image data is acquired, followed by step S13 which encompasses determining the position of the tracking structure in the reference image. Then, step S14 generates the binarized reference image. Subsequent step S15 is directed to selecting the tracking structure from the binarized reference image. Step S16 then continues with generating the binarized planning image, followed by step S17 of selecting the tracking structure from the binarized planning image. Step S18 encompasses generating the template, and step S19 encompasses acquiring the two-dimensional monochrome image. In step S120, the binarization of the monochrome is generated. All the aforementioned steps and/or the data output by those steps serve as an input to step S121 which relates to detecting the position of the tracking structure in the binarized monochrome image.

In the following, an implementation of the method according to the first aspect will be described with reference to FIGS. 2 to 18.

Terminology and abbreviations used in this disclosure are summarized and explained in FIG. 2.

Binary Template Matching

Template Matching is a method for searching and finding the location of a template image in a larger search image. The template image contains the tracking structure which will be searched for. The template image is slid over the search image and compared to the patch of the search image under the template image. The comparison results in a similarity value between the patch and the template. A template mask might be provided to the comparison method to weight the pixels in both the template and the patch. The patch which has the highest similarity with the template is considered as detection result. Its position represents the detected point.

The Binary Template Matching described in this invention preprocesses the search image as described in the section "Image Processing", uses a binary template generated as presented in the section "Binary Template Generation" and a template mask illustrated in the section "Template Mask".

The similarity between the template and a patch in the search image might be computed by the following equation $$R_{TM}(x, y) = \frac{\sum_{x',y'} w(x', y')(1 - |T(x', y') - I(x+x', y+y')|)}{\sum_{x',y'} w(x', y')}$$

with
(x,y)—location of the patch in the image
w—weights as specified in the template mask
T—template image
I—search image.

This is a dedicated similarity measure for comparison of binary images, which has the following properties:
  normalized: $R_{TM} \in [0, 1]$
  computation is faster than cross-correlation
  supports template masks
  clear interpretation of the values:
    $R_{TM}=0$: no similarity
    $R_{TM}=1$: maximum similarity
    $R_{TM}=x$: (x*100)% of the pixels agree (for uniform weights)

Figure 1:
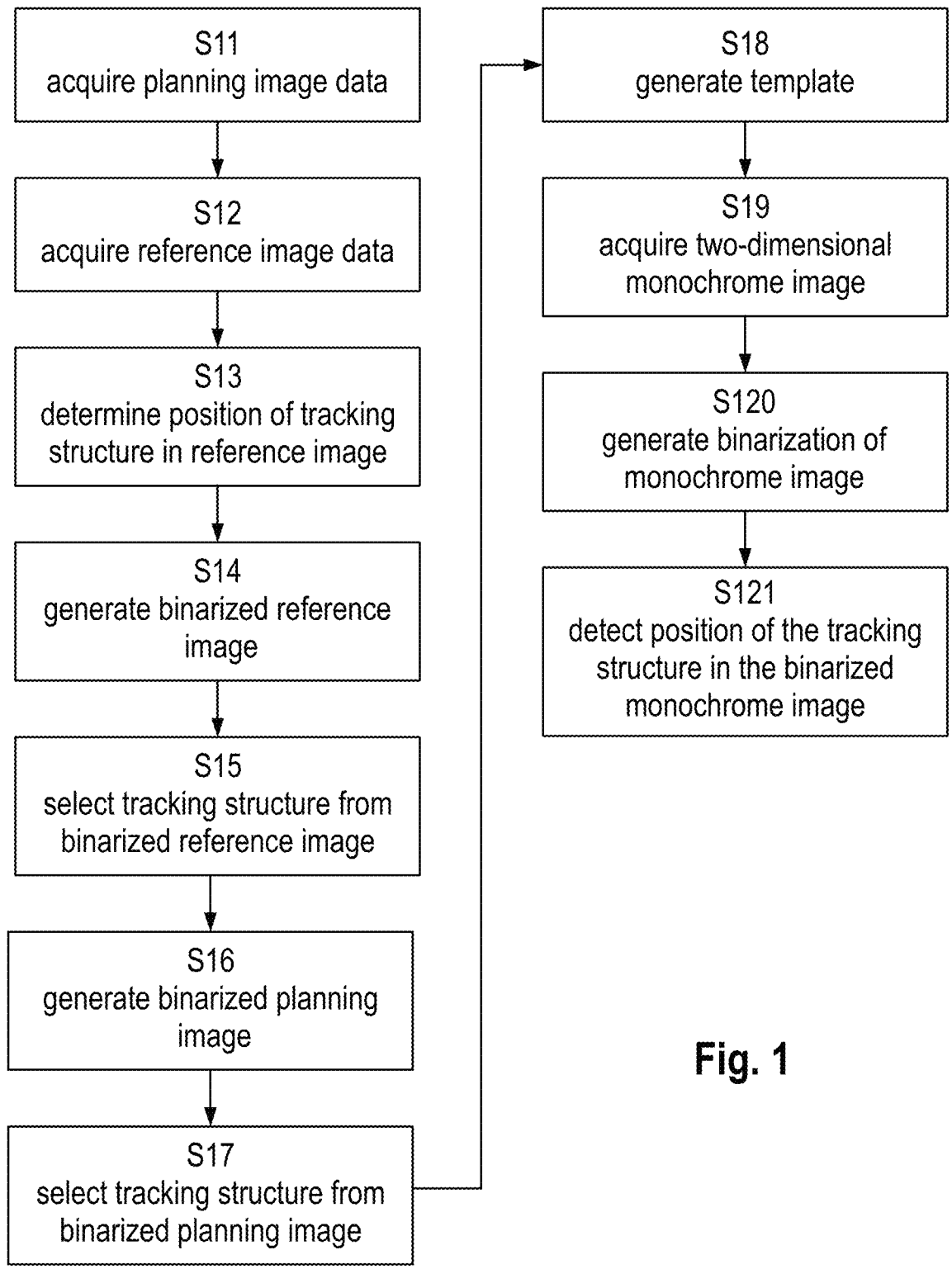
FIG. 1 illustrates a basic flow of the method according to the first aspect.
Figure 3:
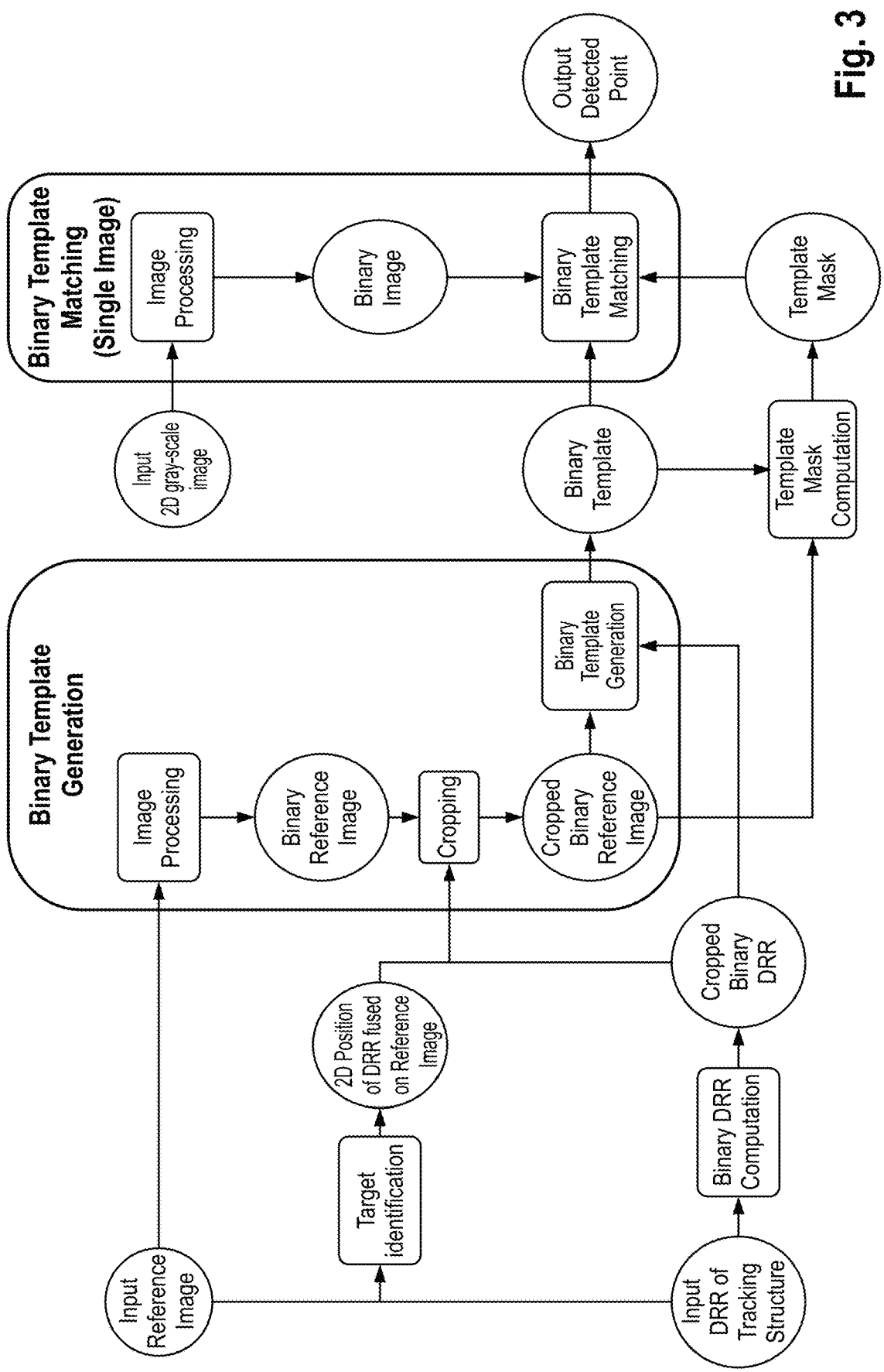
Figure 4:
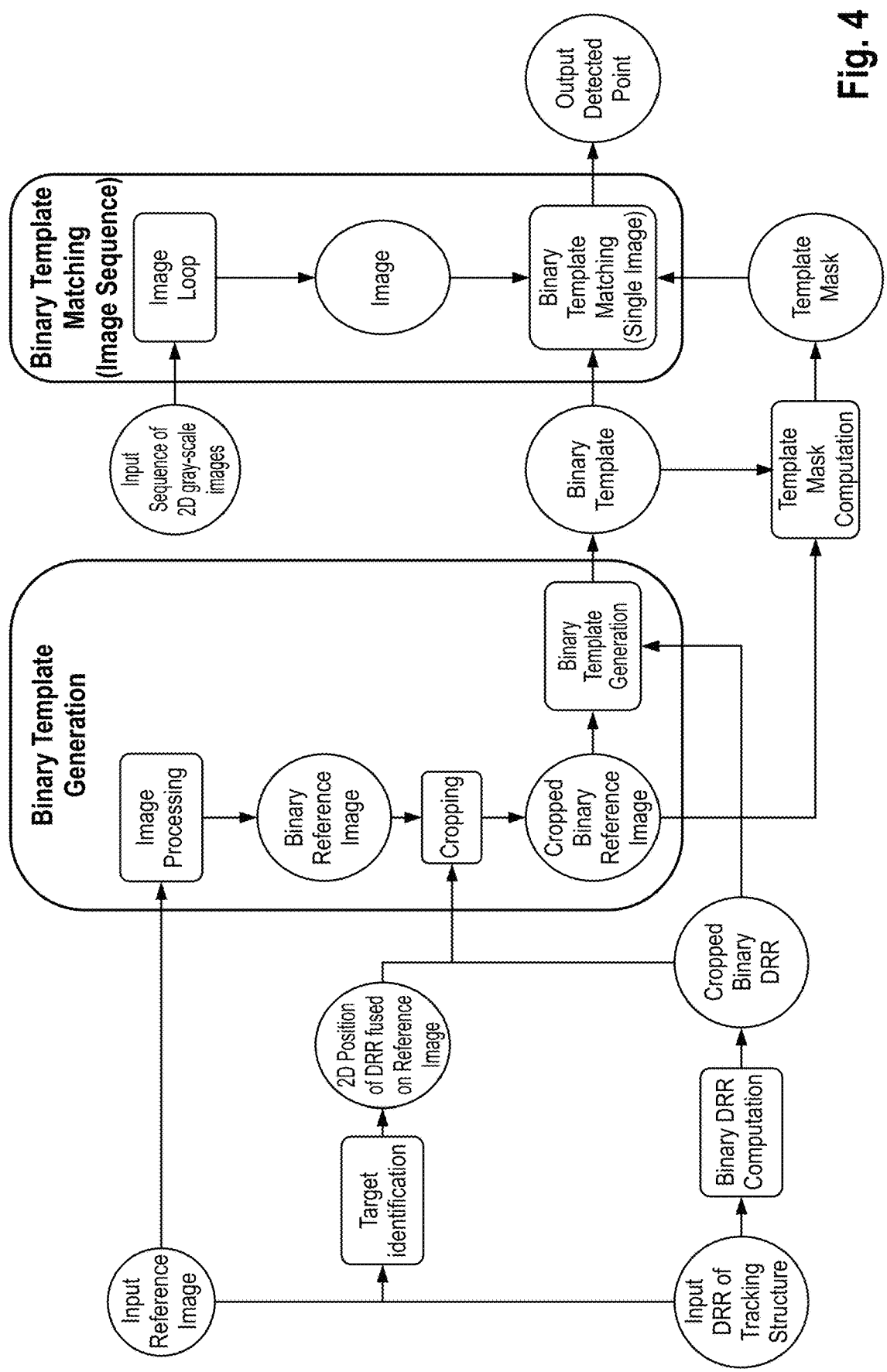
Figure 5:
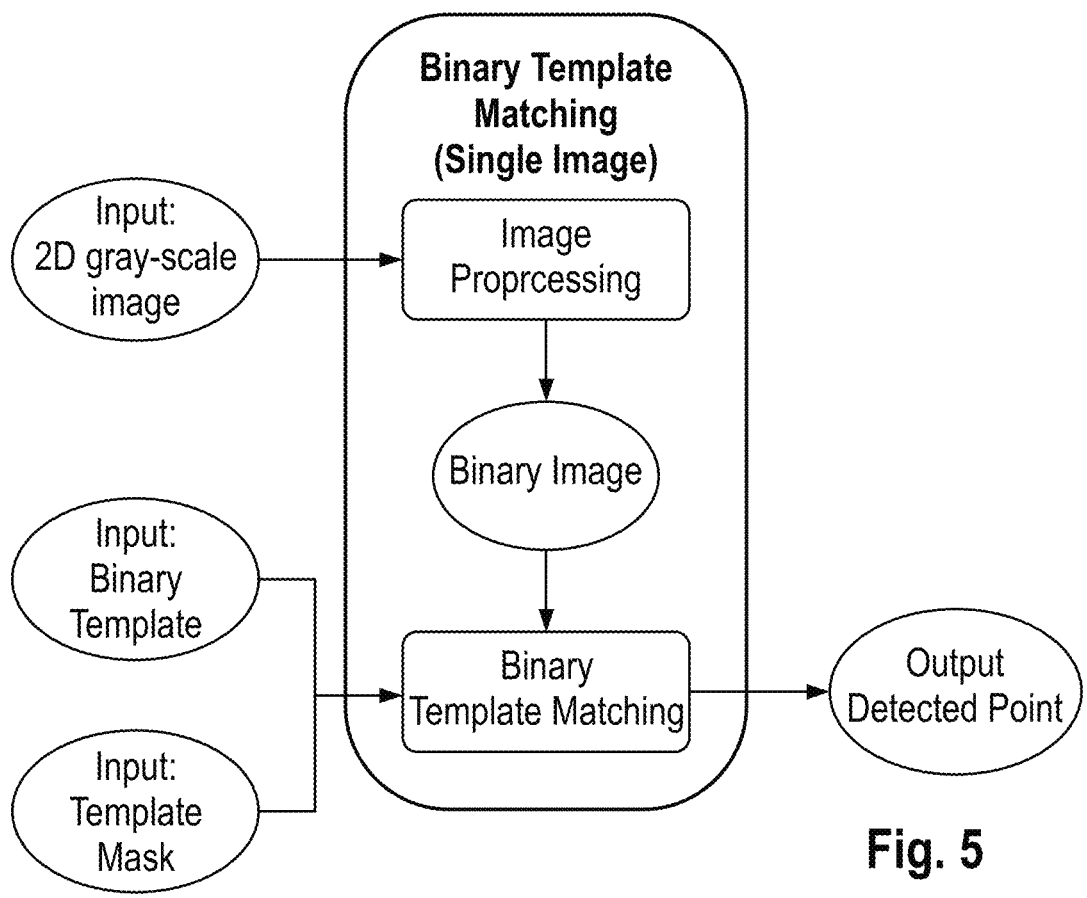

The flow chart of the Binary Template Matching is shown in FIG. 5.

Image Processing

Image processing is performed at two places in the tracking algorithm. First it is used to process the reference image during binary template generation, second to process the incoming search image before performing binary template matching. The used image filters are the same for both processing steps. However, the used parameters might vary (slightly). For the second processing, the knowledge of the binary template might be taken into account to optimize the filter parameters.

Figure 6:
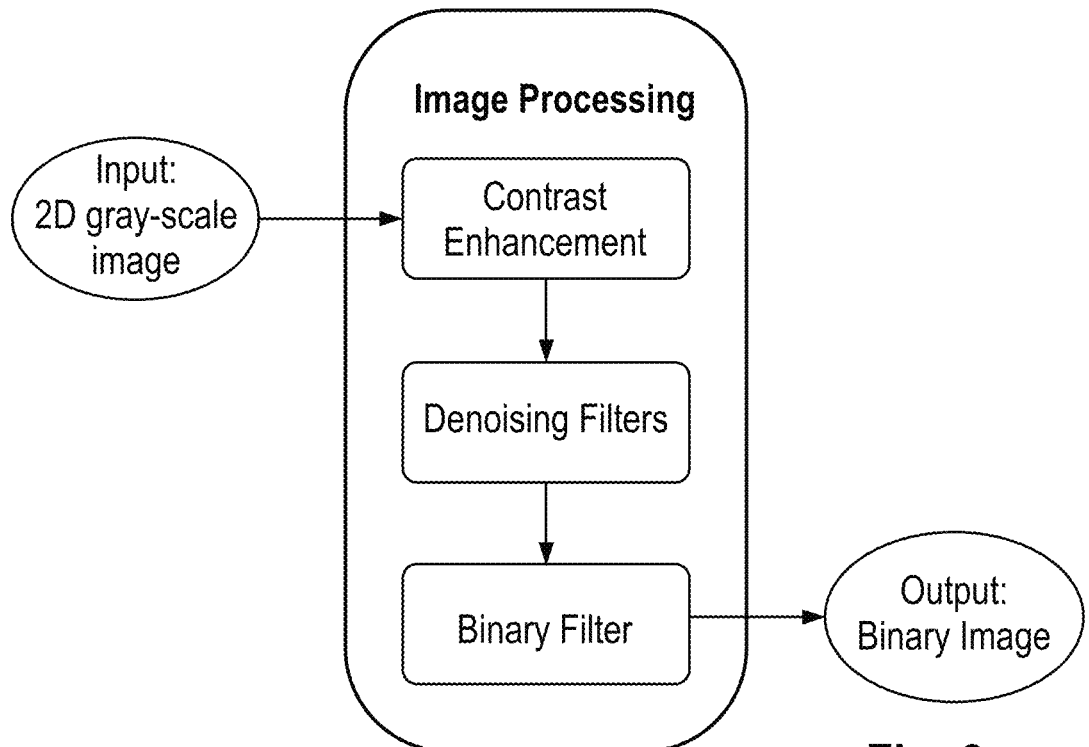

In FIG. 6, the flow chart of the image processing is shown. First the contrast of the image is enhanced by using, e.g., histogram equalization or a CLAHE (Contrast Limited Adaptive Histogram Equalization) filter. Second, a smoothing/denoising filter, e.g. Gaussian filter, might be applied to reduce the image noise (this is an optional feature of the method). Third, a binary filter is applied which transforms the gray-scale image into a binary image by keeping all pixels whose gray value is "darker" (it is assumed without loss of generality that the tracking structure is darker its environment; for x-ray images this means, that air is represented in white) than the environment.

In FIG. 7, the image processing is illustrated for an exemplary incoming x-ray image.

Binary Filter

The binary filter performs the following steps:
1. The local average is computed for every pixel of the input image resulting in a local average image. The kernel of the filter defines the environment of the pixel which is taken to account to compute the local average. The kernel shape and size are parameters of the filter. They might be chosen according to the size and shape of the tracking structure.
2. The local average image is subtracted from the input image resulting in a difference image, in which all pixels which are darker than their environment have negative values.
3. A binary image is obtained by thresholding the difference image. Pixels with a value smaller than the threshold are converted to white and all other pixels are converted to black. The threshold value β is a parameter of the filter. To keep all pixels whose gray value is darker than the environment, a zero threshold has to be chosen, i.e. β=0. Threshold values smaller than zero might be chosen to reduce the influence of noise on the binary image.

Figure 8:
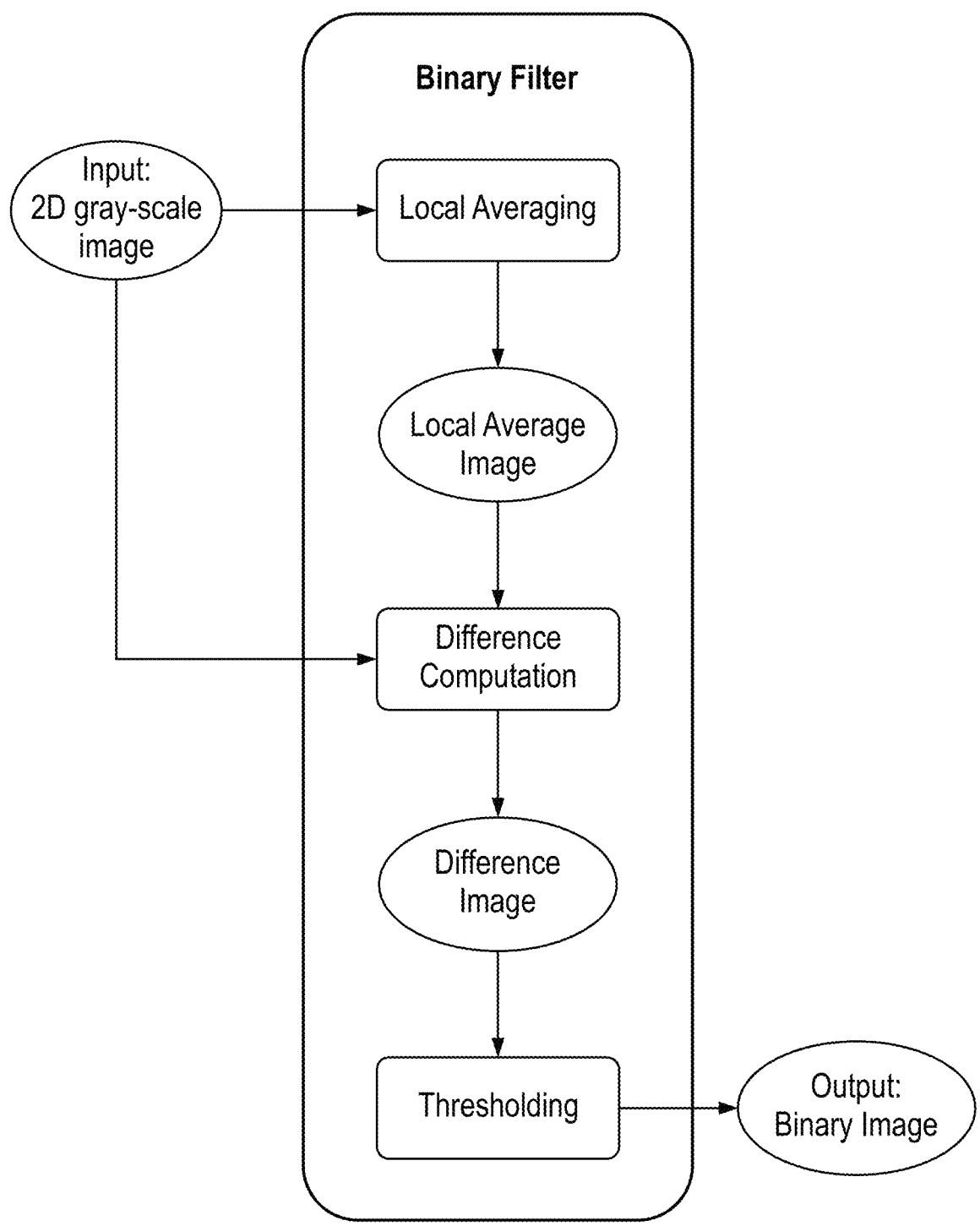

The corresponding flow chart is shown in FIG. 8.

Binary Template Generation

The binary template generation comprises several steps:
1. Target Identification
2. Computation of a cropped binary DRR
3. Computation of a cropped binary reference image
4. Computation of the binary template The first three steps are just preparation steps, and the actual template generation is done in the last step.

All steps are explained in the following in more detail.

Target Identification

Figure 9:
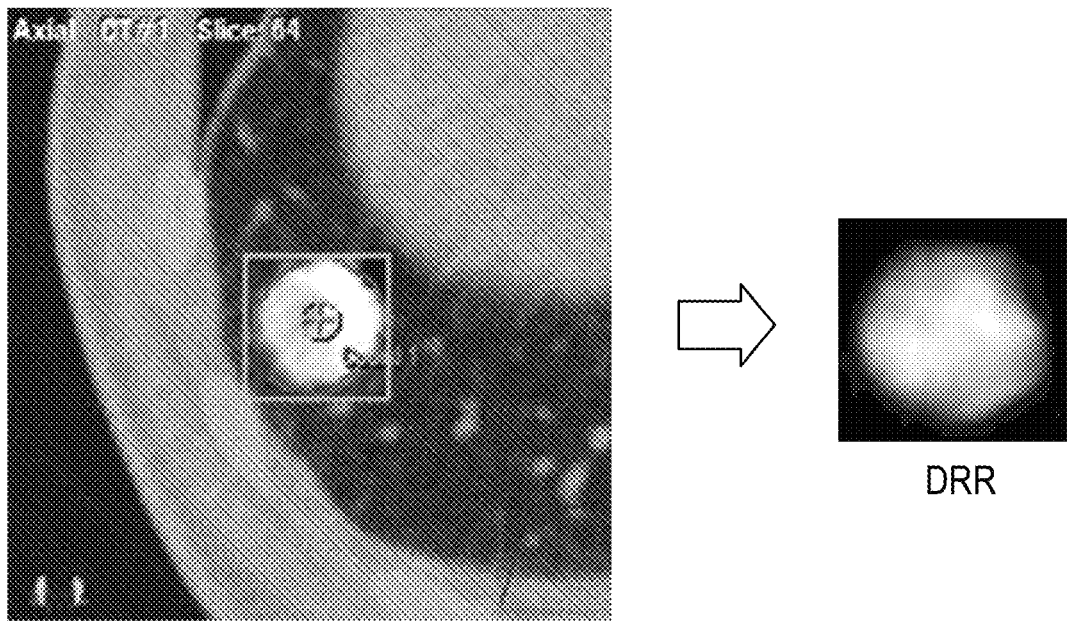

The tracking structure is defined by a physician in the planning CT from which a DRR is rendered, see FIG. 9. The DRR has the same size (width and height) as the images which are considered for tracking. In the following, the term "DRR" always refers to this DRR containing the tracking structure.

From the images which are considered for tracking one image is selected as reference image.

Figure 10:
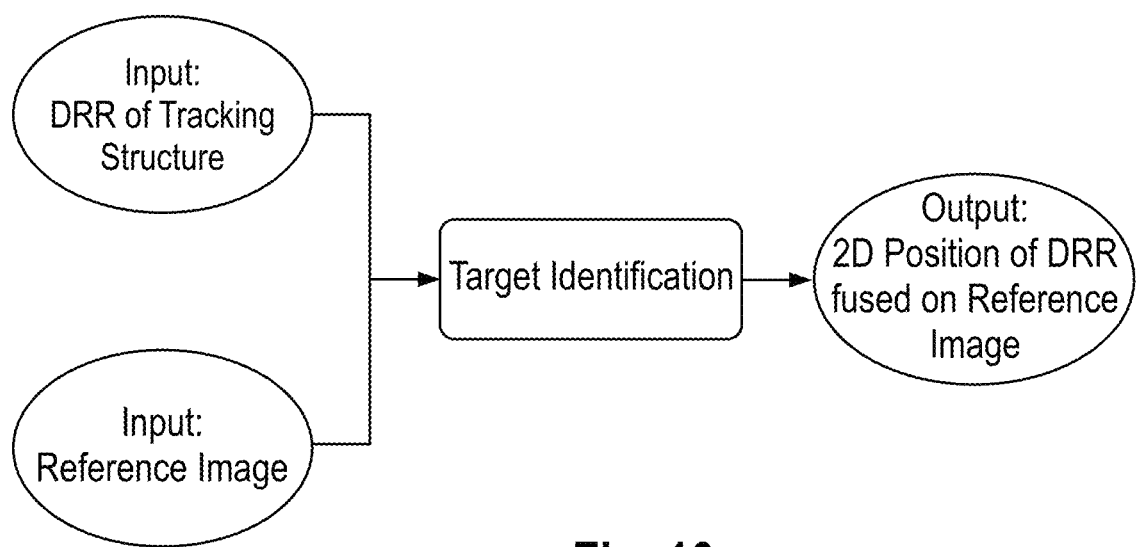

The DRR is fused with this reference image either manually or automatically by using an image fusion algorithm. The fusion results in a 2D shift of the DRR. The flow chart of the Target Identification is shown in FIG. 10

Cropped Binary DRR

The DRR is a gray-scale image which is converted into a binary DRR. The conversion of the gray-scale DRR to a binary DRR might be for example done by simple thresholding $$D_g > \alpha : D_b = 1$$

$$D_g \leq \alpha : D_b = 0$$

With
$D_g$—gray-scale DRR
$D_b$—binary DRR
α—threshold (e.g., α=0)

The created binary DRR depends on the rendering algorithm, the Target Identification and on the tracking structure variability between the time when the planning CT was acquired and the time when the tracking is performed. Therefore, the binary DRR might not appropriately represent the correct shape of the tracking structure.

Two additional binary DRRs are computed, one which is larger than the original binary DRR (maximum DRR) and one which is smaller than the original DRR (minimum DRR). The correct tracking contour is expected to be located between the contour of the maximum and the minimum DRR. The distance of the contour of the maximum (minimum) DRR to the contour of the original binary DRR is the parameter $\gamma_{max}$ ($\gamma_{min}$) of the algorithm which describes the expected maximum uncertainty of the DRR being too small (large). The maximum (minimum) DRR is created by morphological dilation (erosion) of the original binary DRR.

A bounding box $B_{crop}$ is computed for the maximum DRR which is the smallest rectangle enclosing all non-zero pixels. All three binary DRRs (original, maximum and minimum) are cropped with this bounding box.

Cropped Binary Reference Image

The reference image is converted into a binary reference image with the image processing presented in the section "Image Processing".

A cropping rectangle is computed by shifting the bounding box $B_{crop}$ computed as explained above in the section "Cropped Binary DRR" by the fusion shift obtained during target identification, as explained above in the section "Target Identification". Hence, the cropping rectangle is the bounding box of the maximum DRR transformed to the reference image. The binary reference image is cropped with the cropping rectangle resulting in the Cropped Binary Reference Image.

Binary Template Generation

The binary template is computed from the Cropped Binary DRR (see section "Cropped Binary DRR") and the Cropped Binary Reference Image ("CBRI") (see section "Cropped Binary Reference Image").

The Cropped Binary DRR is considered as first guess of the Binary Template. This preliminary binary template ("PBT") is improved by comparison with the CBRI. The idea is to change the contours of the PBT such that the agreement with the contours of the CBRI is maximal. The contour of the corrected PBT ("CPBT") is then considered as contour of the final binary template. This procedure is illustrated in FIG. 12.

However, the contours present in the CBRI might not completely correspond to the correct contour of the tracking structure. The reasons for that might be:
Tracking structure is occluded by another structure (for example a rib is occluding a lung tumor which should be tracked).
Bad contrast of the tracking structure.

This situation is sketched in FIG. 13. To handle these situations, a dedicated algorithm for improvement of the PBT contour is used instead of just taking the contours as present in the CBRI. FIG. 13 is similar to FIG. 12 but was generated for a slightly different CBRI. In FIG. 13, contour estimation is necessary and the CBT f) differs from the CBRI b).

Figure 14:
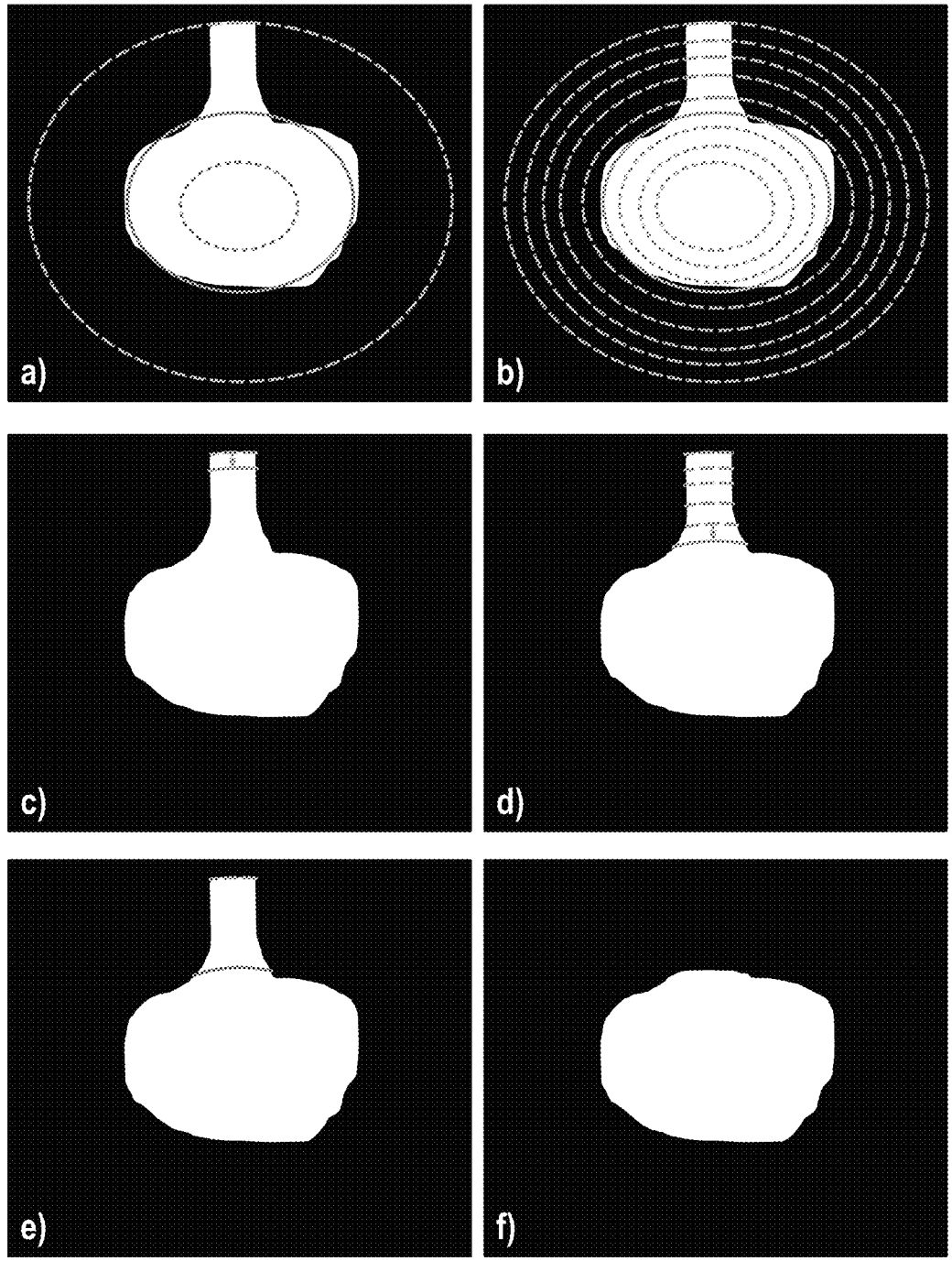

FIG. 14 illustrates the principle of contour estimation applied in this implementation of the method according to the first aspect, wherein sub-figures a) to f) can be described as follows:
sub-figure a): CBRI with DRR contour (solid line), maximal eroded DRR contour (dotted line) and maximal dilated DRR contour (dashed line);
sub-figure b): CBRI with set of dilated and eroded contours;

sub-figure c): maximal dilated DRR contour inside the CBRI (dashed line) and first guess of estimated contour (solid line)—this is the first iteration step;

sub-figure d): several dilated DRR contours (dashed lines) which were tested as estimated contour and winning estimated contour (solid line);

sub-figure e): estimated contour on CBRI; and sub-figure f): corrected CBRI where the correction is based on the estimated contour.

The idea of this algorithm is that it notices when some contour information is missing in the CBRI. In these cases it uses the information about the shape of the tracking structure from the DRR to estimate the missing contours.

Figure 15:
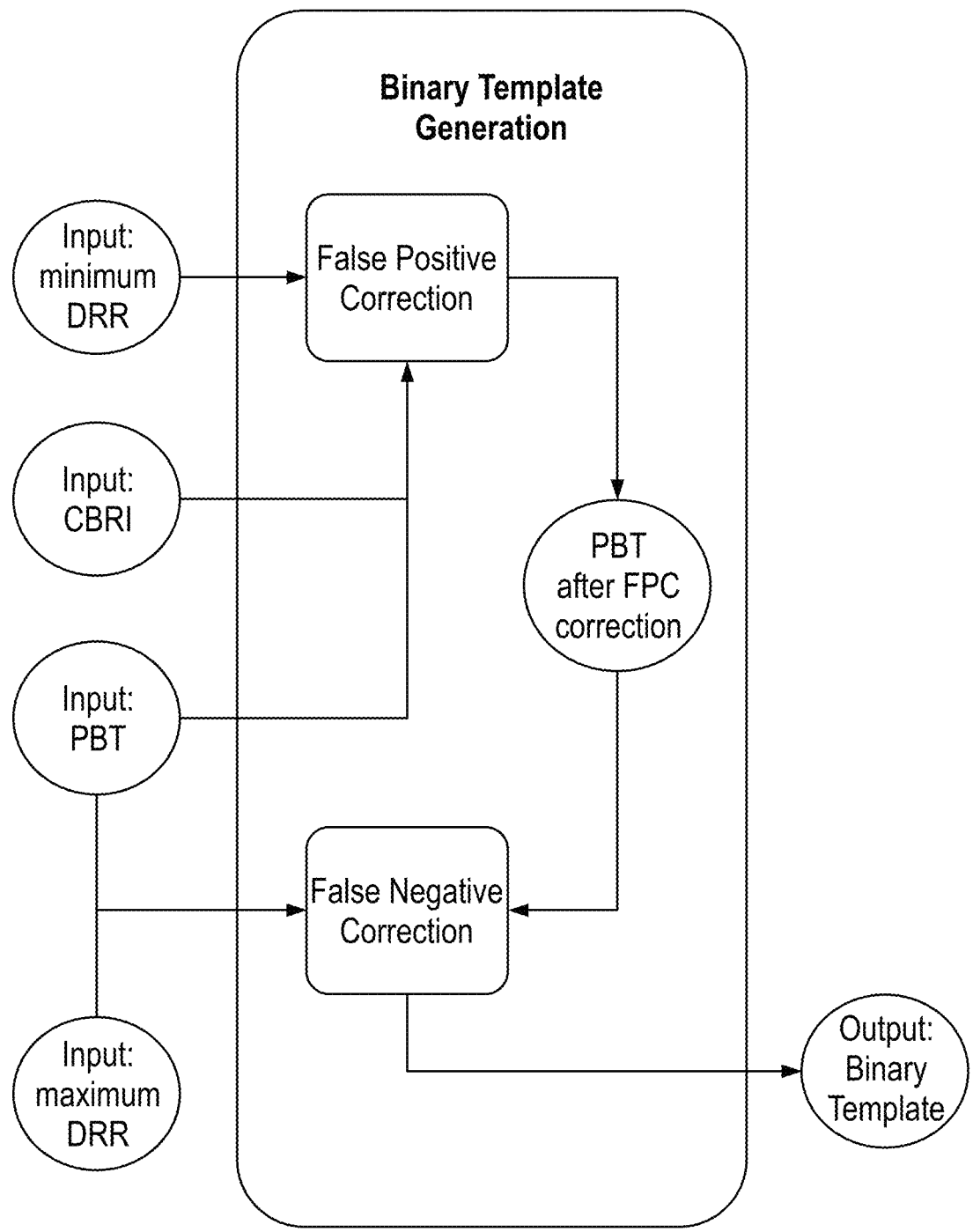

The improvement of the PBT is done in two steps. First all pixels which are contained in the PBT but not in the CBRI are corrected. These pixels are called "false positives" and the corresponding correction is called "false positive correction". Only pixels which are not contained in the minimum DRR are corrected as no correction inside the minimum DRR is expected (see section "Cropped Binary DRR"). The result of the false positive correction is a corrected PBT ("CPBT"). Second all pixels which are not contained in the CPBT but in the CBRI are corrected. These pixels are called "false negatives" and the corresponding correction is called "false negative correction". Only pixels inside the maximum DRR are corrected as no correction outside the maximum DRR is expected (see again section "Cropped Binary DRR"). The result of the false negative correction is the final binary template. The corresponding flow chart is shown in FIG. 15.

Figure 16:
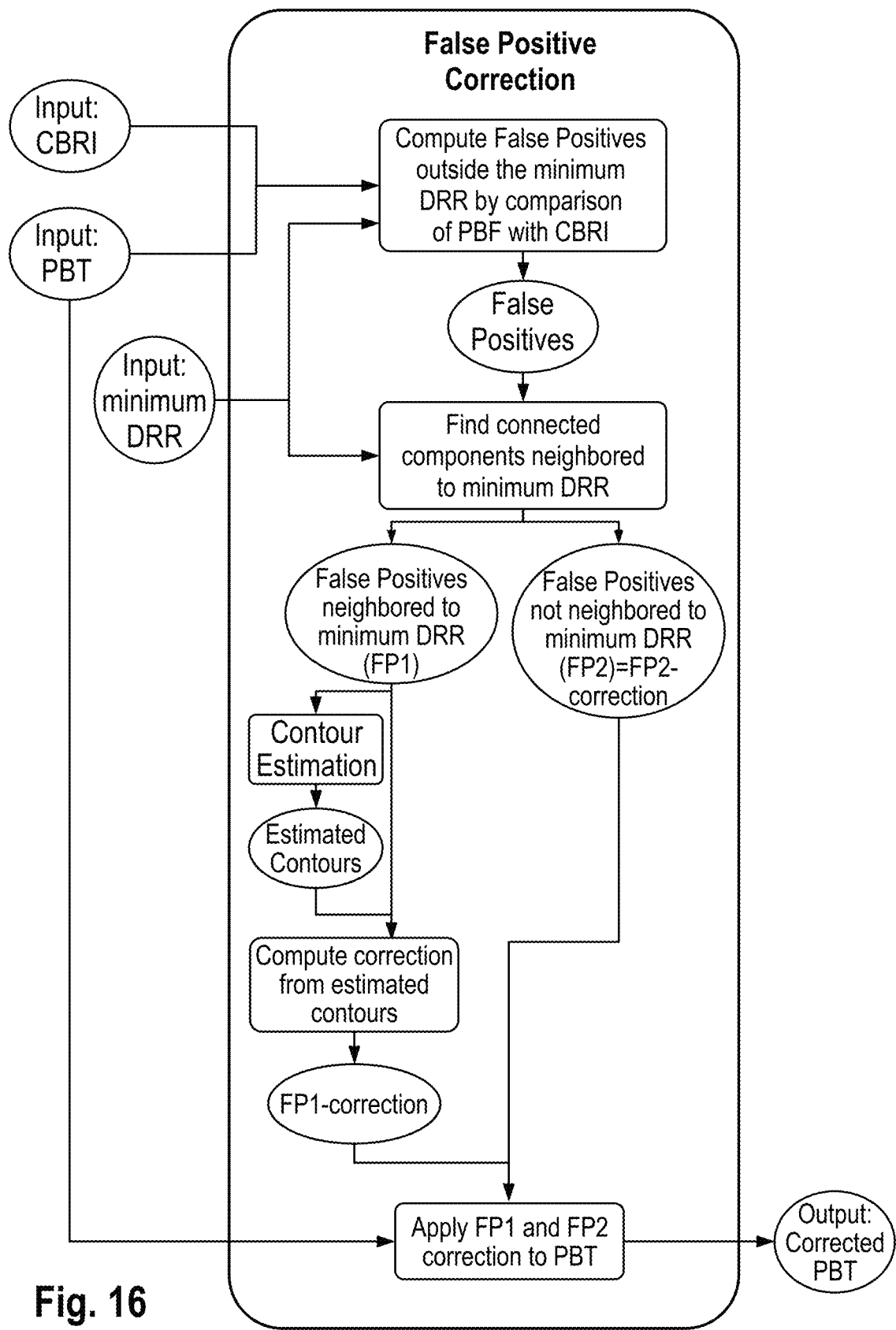

The flow chart of the false positive correction is shown in FIG. 16. First all false positives outside the minimum DRR are identified. Then all connected components of the false positives are computed which are sorted into two categories
1. FP1: false positives neighbored the minimum DRR
2. FP2: false positives not neighbored the minimum DRR The components belonging to the first category have to be analyzed further as there is apparently no contour information in the CBRI. Therefore, the missing contours are estimated and from the estimated contours the corrections are computed. This procedure will be explained below in more detail. The components belonging to the second category are directly considered as corrections. All corrections are collected into a correction image which is then subtracted from the PBT resulting in the corrected preliminary binary template (CPBT).

Figure 17:
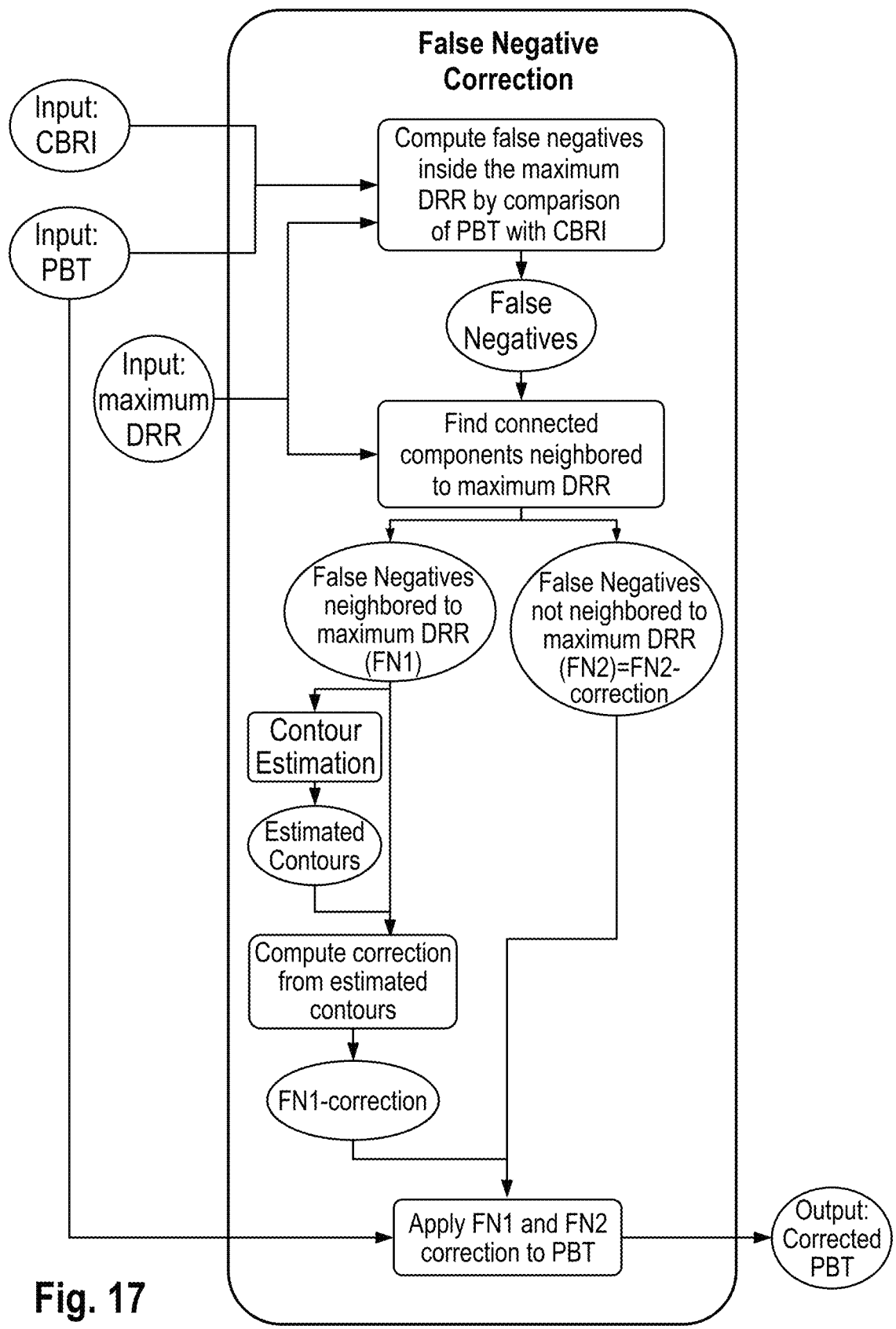

The flow chart of the false negative correction is shown in FIG. 17. The principle is very similar to the false positive correction except that false negatives instead of false positives and the maximum DRR instead of the minimum DRR is considered. The computed correction image is then added to the CPBT resulting in the final binary template.

The contour estimation used in both the false positive and false negative correction is working as follows:
1. A ordered set of contours $S_{contours}$ is computed from the binary DRR by morphological erosion (dilation) with kernel sizes $\{3, 5, \ldots, 2*\gamma_{min}+1\}$ ($\{3, 5, \ldots, 2*\gamma_{max}+1\}$) in case of false positive (negative) correction. The last contour in the set corresponds to the contour of the minimum (maximum) DRR.
2. For every connected component in FP1 (FN1) a specific contour set $S_{specific}$ is created by multiplying every contour in the set $S_{contours}$ with the connected component.
3. Then for every connected component, the contour is estimated by iterating backwards over the contours in $S_{specific}$ (starting with the contour following the contour in the set which is farthest away from the binary DRR contour) and checking for every contour:
   1. Are the end-points of the contour located on the contour of the CBRI?
      "yes": continue with check 2
      "no": stop iteration
   2. Is its length shorter than the previous contour?
      "yes": accept contour and continue
      "no": check: Is its length increase below a threshold value?
         "yes": accept contour and continue
         "no": stop iteration
   4. The last accepted contour is considered as estimated contour.

This approach gives the optimum contour which is on the one hand as close as possible to the contour of the binary DRR and on the other hand as far away as necessary from the contour of the binary DRR to represent a connection between two points of the contour of the CBRI. Additionally, the shape of the estimated contour is "natural" as it is determined by the binary DRR contour. For every connected component, the computed estimated contour is used to split the connected component into two parts: one which is neighbored to the binary DRR and one which is neighbored to the minimum (maximum) DRR. The former is considered for the FP1 (FN1) correction.

Figure 11:
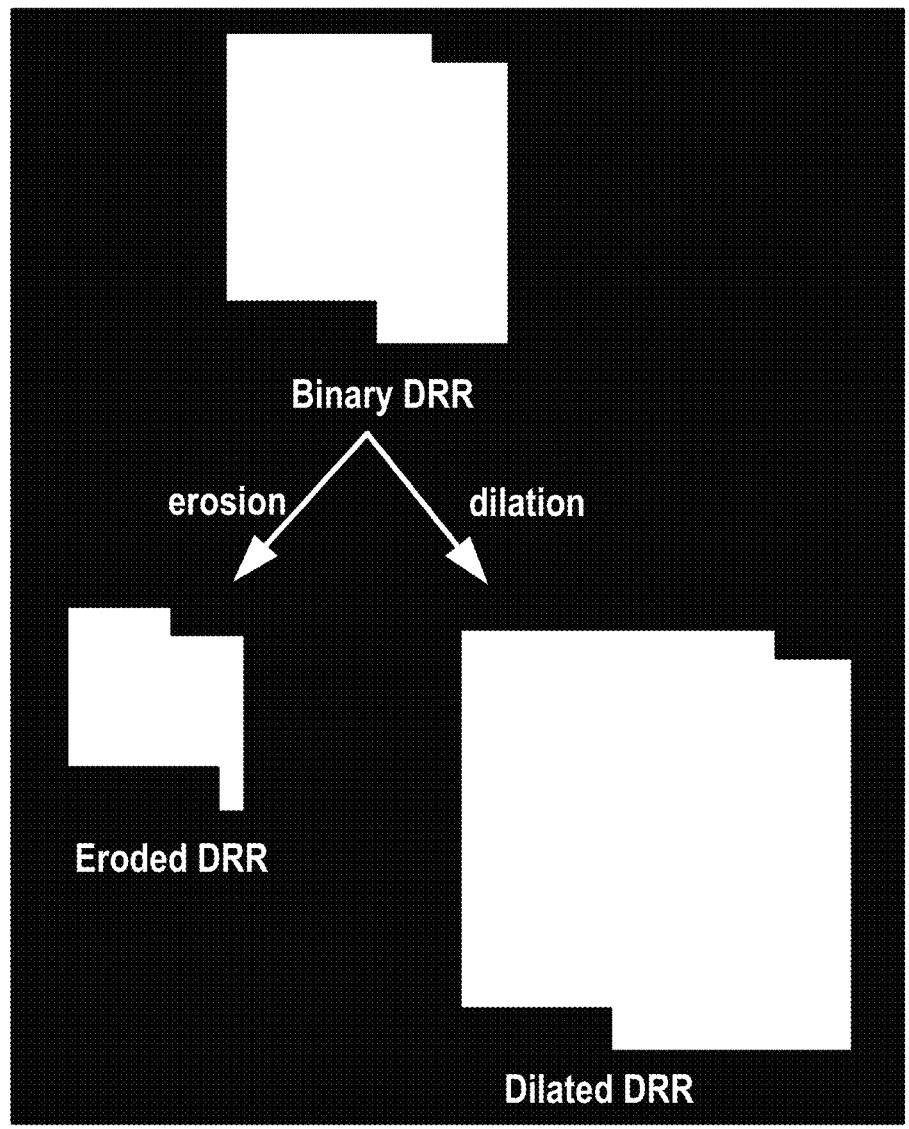

FIG. 11 illustrates the computation of the eroded and dilated DRR. The eroded DRR is also called "minimum DRR" and the dilated DRR is also called "maximum DRR".

Template Mask

The idea is to compute a template mask, which has the following properties:
1. The mask weights the pixels close to the contour of the binary template higher than pixels far away from the contour as the probability of the former being correctly represented in the binary search image is higher as for the latter (this depends on the binary filter parameters).
2. The mask weights the pixels close to known contours of the binary template higher than pixels close to estimated contours of the binary template.

From the binary template a binary mask is created by morphological dilation of the binary template. With this, the mask contains both the tracking structure plus some background information. Then for every pixel in the binary mask the distance transform is computed which is the closest distance to a black—pixel. Depending on the distance, the weight of the pixel is computed from an approximation of the Heaviside function, in which distances close to zero (i.e., close to the contour of the binary template) approximate an upper weight $w_{up}$ and distances far away from zero (i.e., close to the inner of the binary template) approximate a lower weight $w_{low}$. Choosing values for the weights such that $w_{up} > w_{low}$ leads to a mask which fulfills the first property in the list above.

Additionally, the values of all pixels in the mask whose value is different than the corresponding value in CBRI are set to the lower weight $w_{low}$. With this, also the second property from the list above is fulfilled.

Figure 18:
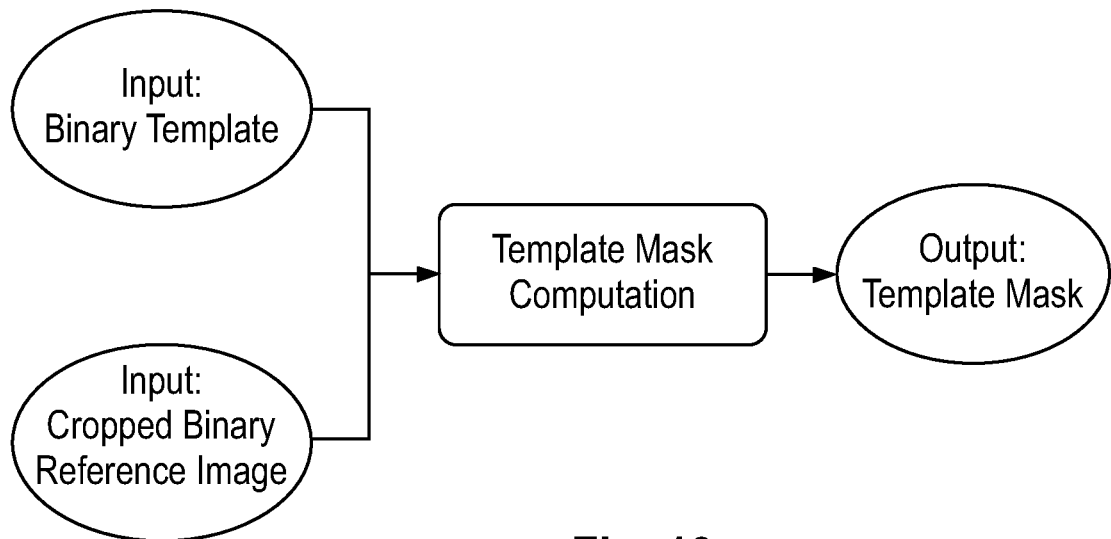

The flow chart for the template mask computation is shown in FIG. 18.

Figure 19:
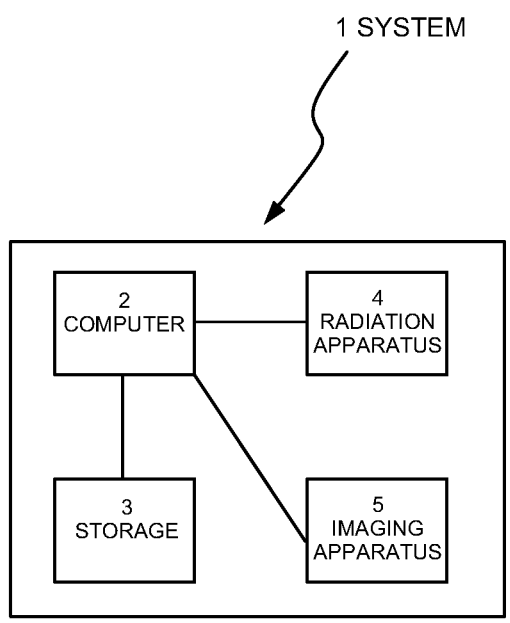
FIG. 19 is an illustration of the system according to the fifth aspect.

FIG. 19 illustrates the basic setup of the system 1 according to the fifth aspect. The system 1 comprises a computer 2 which is configured to run a program which causes the computer to execute the method according to the first aspect. The computer 2 is operably coupled to a non-transitory data storage device 3, a medical imaging apparatus 5 (such as a flat panel x-ray imaging system) and a radiation treatment apparatus 4 comprising a treatment beam source and patient support unit. In an example of the system 1, the medical imaging device 5 may be part of the radiation treatment apparatus.

The disclosed invention can be summarized as follows:

The Binary Tracking presented in this application has the following specific features which distinguish this solution over the prior art:
1. Binary template based on the reference image.
2. Image processing of the input search image resulting in a binary search image The technical effects of the above two features are at least the following:

Occluding structures do not affect the template or at least their impact on the template is reduced, as the template is binary.

The similarity between the binary template and the corresponding patch of a binary search image with a motion state different than the one of the reference image will be ideally maximal. At least the similarity is higher as if gray-scale images would have been considered.

Mono-modal template matching as both the template and the search image are binary images.

Template is up-to-date as it is created from one of the images of the image sequence.

In summary, tracking failure is more unlikely with the presented features, i.e. the robustness of tracking is increased.

The invention claimed is:

1. A computer-implemented method for determining a position of an anatomical tracking structure in a tracking image usable for controlling a radiation treatment of a patient, the computer-implemented method comprising:
    acquiring planning image data, which describes a planning image of the anatomical tracking structure;
    acquiring reference image data, which describes a reference image of the anatomical tracking structure;
    determining a position of the anatomical tracking structure in the reference image;
    generating a binarized reference image from the reference image through a binarization of the reference image;
    making a selection from the binarized reference image based on the position of the anatomical tracking structure in the reference image, wherein the selection includes the anatomical tracking structure;
    processing the planning image to generate at least one binarized planning image being a binarization of the planning image;
    determining the position of the anatomical tracking structure in the at least one binarized planning image and making a selection from the at least one binarized planning image, wherein the selection from the at least one binarized planning image includes the anatomical tracking structure;
    generating a template for determining the position of the anatomical tracking structure in another image based on the selection from the binarized reference image and the selection from the at least one binarized planning image;
    acquiring a two-dimensional monochrome image, which describes the anatomical tracking structure;
    processing the two-dimensional monochrome image to generate a binarized two-dimensional monochrome image being a binarization of the two-dimensional monochrome image; and
    detecting the position of the anatomical tracking structure in the binarized two-dimensional monochrome image by matching the template with the binarized two-dimensional monochrome image.

2. The computer-implemented method according to claim 1, further comprising:
    processing the reference image comprises computing, for each pixel in the reference image, a local average of colour values in a neighbourhood, of each pixel in the reference image, thereby generating a local average image describing the local average of colour values for each pixel.

3. The computer-implemented method according to claim 2, further comprising:
    comparing the local average image to the reference image to generate a difference image, which describes, for each pixel of the reference image and each pixel of the local average image, a difference between a colour value of a respective pixel in the reference image and a local average of the respective pixel in the reference image.

4. The computer-implemented method according to claim 3, wherein the generating the binarized reference image from the reference image through the binarization of the reference image comprises thresholding the difference image by a colour value.

5. The computer-implemented method according to claim 2, wherein the determining the position of the anatomical tracking structure in the reference image comprises a user interaction or automatically and/or a selection from the at least one binarized planning image includes pixels in the at least one binarized planning image having a colour value with a predetermined relationship to a predetermined threshold colour value.

6. The computer-implemented method according to claim 5, further comprising:
    correcting a colour value, which is contained in the template but not in the selection from the binarized reference image, by adapting a contour of the template to a geometry of the selection from the binarized reference image.

7. The computer-implemented method according to claim 1, further comprising:
    correcting a colour value, which is contained in the selection from the binarized reference image but not in the template, by adapting a contour of the template to a geometry of the selection from the binarized reference image.

8. The computer-implemented method according to claim 1, further comprising:
    generating a template mask based on the template, wherein the template mask is configured by morphological dilation or morphological erosion of the template.

9. The computer-implemented method according to claim 8, wherein the generating the template mask based on the template comprises generating the template mask by a morphological dilation and/or a morphological erosion of the template.

10. The computer-implemented method according to claim 1, further comprising:
    acquiring a series of two-dimensional monochrome images;
    processing each of the series of two-dimensional monochrome images to generate a binarized two-dimensional monochrome image being a binarization for each of a respective two-dimensional monochrome image; and detecting the position of the anatomical tracking structure in each of the respective binarized two-dimensional monochrome image by matching the template with the respective binarized two-dimensional monochrome image.

11. The computer-implemented method according to claim 1, further comprising:

at least one of:
- a relative position between an anatomical tracking structure of the radiation treatment, and adjusting at least part of a radiation treatment system for performing the radiation treatment based on the position of the anatomical tracking structure in the binarized two-dimensional monochrome image; or
- determining a control signal based on the position of the anatomical tracking structure in the binarized two-dimensional monochrome image, and issuing the control signal to a treatment beam source of the radiation treatment apparatus for controlling an emission of a treatment beam.

12. The computer-implemented method according to claim 1, wherein the planning image and the reference image are of different imaging modality, and further including matching the planning image and the reference image with a multimodal atlas configured to match different imaging modalities onto on another, and establishing a positional transformation between the planning image and the reference image based on a match between the planning image and the multimodal atlas and a match between the reference image and the multimodal atlas.

13. A non-transitory computer-readable storage medium storing computer instructions executable by one or more processors to perform a method comprising:

acquiring planning image data, which describes a planning image of an anatomical tracking structure;

acquiring reference image data, which describes a reference image of the anatomical tracking structure;

determining a position of the anatomical tracking structure in the reference image;

generating a binarized reference image from the reference image through a binarization of the reference image;

making a selection from the binarized reference image based on the position of the anatomical tracking structure in the reference image, wherein the selection includes the anatomical tracking structure;

processing the planning image to generate at least one binarized planning image being a binarization of the planning image;

determining the position of the anatomical tracking structure in the at least one binarized planning image and making a selection from the at least one binarized planning image, wherein the selection from the at least one binarized planning image includes the anatomical tracking structure;

generating a template for determining the position of the anatomical tracking structure in another image based on the selection from the binarized reference image and the selection from the at least one binarized planning image;

acquiring a two-dimensional monochrome image, which describes the anatomical tracking structure;

processing the two-dimensional monochrome image to generate a binarized two-dimensional monochrome image being a binarization of the two-dimensional monochrome image; and detecting the position of the anatomical tracking structure in the binarized two-dimensional monochrome image by matching the template with the binarized two-dimensional monochrome image.

14. A system for determining a position of an anatomical tracking structure in a tracking image usable for controlling a radiation treatment such as at least one of radiotherapy or radiosurgery of a patient, the system comprising:

at least one computer having a memory and at least one processor connected to the memory, the memory having instructions stored thereon for performing a method comprising:

acquiring planning image data, which describes a planning image of the anatomical tracking structure;

acquiring reference image data, which describes a reference image of the anatomical tracking structure;

determining a position of the anatomical tracking structure in the reference image;

generating a binarized reference image from the reference image through a binarization of the reference image;

making a selection from the binarized reference image based on the position of the anatomical tracking structure in the reference image, wherein the selection includes the anatomical tracking structure;

processing the planning image to generate at least one binarized planning image being a binarization of the planning image;

determining the position of the anatomical tracking structure in the at least one binarized planning image and making a selection from the at least one binarized planning image, wherein the selection from the at least one binarized planning image includes the anatomical tracking structure;

generating a template for determining the position of the anatomical tracking structure in another image based on the selection from the binarized reference image and the selection from the at least one binarized planning image;

acquiring a two-dimensional monochrome image, which describes the anatomical tracking structure;

processing the two-dimensional monochrome image to generate a binarized two-dimensional monochrome image being a binarization of the two-dimensional monochrome image; and detecting the position of the anatomical tracking structure in the binarized two-dimensional monochrome image by matching the template with the binarized two-dimensional monochrome image;

at least one electronic data storage device storing at least the planning image data;

a medical imaging device for generating the two-dimensional monochrome image;

a radiation treatment apparatus comprising a treatment beam source and a patient support unit;

wherein the at least one computer is coupled to:

the at least one electronic data storage device for acquiring, from the at least one data storage device, at least the planning image data; to the medical imaging device for acquiring, from the medical imaging device, the two-dimensional monochrome image;

to the radiation treatment apparatus for issuing a control signal to the radiation treatment apparatus for controlling at least one of:

a functionality of the treatment beam source; or
a position of the patient support unit on a basis of the position of the anatomical tracking structure in the binarized two-dimensional monochrome image.

* * * * *